United States Patent [19]

Suzuki et al.

[11] 3,960,976
[45] June 1, 1976

[54] METHOD FOR THE SEPARATION OF HYDROCARBONS

[75] Inventors: Yoshiaki Suzuki, Machida; Hajime Mori; Takemi Nakanome, both of Yokohama, all of Japan

[73] Assignee: Mitsubishi Chemical Industries Ltd., Tokyo, Japan

[22] Filed: June 5, 1973

[21] Appl. No.: 367,295

[30] Foreign Application Priority Data

| June 5, 1972 | Japan | 47-55745 |
| June 26, 1972 | Japan | 47-63780 |
| July 6, 1972 | Japan | 47-67737 |
| July 13, 1972 | Japan | 47-70253 |
| Aug. 2, 1972 | Japan | 47-77400 |

[52] U.S. Cl. .......................... 260/674 R; 208/308; 260/669 A; 260/674 A; 260/674 SE; 260/674 N; 260/677 A; 260/681.5 C
[51] Int. Cl.² ............................................ C07C 7/01
[58] Field of Search ...... 260/674 R, 674 SE, 674 N, 260/674 A, 669 A, 675, 677 A, 681.5 C, 666 A; 208/308

[56] References Cited
UNITED STATES PATENTS

| 2,973,394 | 2/1961 | Atkinson et al. | 260/669 |
| 3,201,489 | 8/1965 | Knaack | 260/674 |
| 3,217,052 | 11/1965 | Meek et al. | 260/669 |
| 3,401,112 | 9/1968 | Dunlop et al. | 208/308 |
| 3,755,487 | 8/1973 | Jahnig et al. | 260/677 |

FOREIGN PATENTS OR APPLICATIONS

| 987,065 | 3/1965 | United Kingdom | 260/674 |

*Primary Examiner*—Delbert E. Gantz
*Assistant Examiner*—C. E. Spresser
*Attorney, Agent, or Firm*—Sughrue, Rothwell, Mion, Zinn & Macpeak

[57] ABSTRACT

Hydrocarbons are reacted with a tri-halogenoacetate of the formula

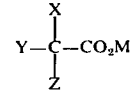

wherein X, Y and Z each represents a halogen atom and M represents a mono valent metal of group Ib to form the corresponding complexes, and then the thus formed complexes are decomposed to selectively separate the desired hydrocarbon components. The used tri-halogenoacetate also is recovered by the decomposition of the complexes.

42 Claims, No Drawings

METHOD FOR THE SEPARATION OF HYDROCARBONS

BACKGROUND OF THE INVENTION

1. Field of the Invention

This invention relates to a method for separating hydrocarbons, and more precisely, a method for separating specifically determined hydrocarbons from other hydrocarbons as well as for separating the specified hydrocarbons into the respective structural isomers.

2. Description of the Prior Art

Aromatic hydrocarbons such as xylene, styrene, etc., olefins and some other kinds of condensed polycyclic hydrocarbons are extremely important in the field of petrochemical industries in these days as raw materials of synthetic resins, synthetic rubbers and other high molecular compounds and as raw materials of various kinds of derivatives, and these hydrocarbon substances are obtained from feed materials such as petroleum products, cracked gasolines, tar products, etc. for example by means of distillation or the like. For example, xylene is separated in general from petroleum reformates, etc. as mixed xylene by means of various kinds of distillation operations, and the thus obtained mixed xylene is further separated into the respective isomers by means of various methods and the thus separated isomers are collected. As the method for separating the mixed xylene into the respective isomers, various kinds of methods have been known, for example, fractional distillation, solvent extraction, adsorption chromatography, low-temperature processing, etc. However, all these methods require very complicated operations.

Olefinic hydrocarbons of four or more carbon atoms have various kinds of isomers, and these hydrocarbons are separated into the respective isomers by means of precision fractional distillation, extraction, extractive distillation, adsorption chromatography by molecular sieves, etc. Condensed polycyclic hydrocarbons are separated from tar products, petroleum products, etc. as raw materials by means of precision fractional distillation, extraction, crystallization, etc. after a light oil fraction has been distilled and separated. However, these methods require fairly complicated steps and the operation thereof also is fairly troublesome.

The inventors have studied the separation of hydrocarbons and as a result have found that a tri-halogenoacetate of a mono valent metal of group IB of the Periodic Table may form complexes with certain kinds of hydrocarbons, that the complex forming ability of the tri-halogenoacetate varies, depending upon the kinds of hydrocarbons, and that the formed complexes may easily be decomposed by means of water or heat to recover the hydrocarbons and the tri-halogenoacetate. On these grounds, the inventors have attained a new technical art to separate and purify various kinds of hydrocarbons by using the formation of complexes with the tri-halogenoacetate of a mono valent metal of group IB.

SUMMARY OF THE INVENTION

The object of the present invention is to provide a new method for separating and purifying hydrocarbons.

Another object of the present invention is to provide a method for separating hydrocarbons by forming complexes of hydrocarbons and a tri-halogenoacetate of a mono valent metal of group Ib and then decomposing the formed complexes.

Still another object of the present invention is to provide a method for separating hydrocarbons into the respective structural isomers.

DETAILED DESCRIPTION OF THE INVENTION

The tri-halogenoacetate which may form complexes with hydrocarbons and which is used in the present invention is represented by the following formula:

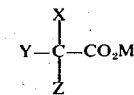

wherein X, Y and Z each represents a halogen atom, and M represents a mono valent metal of group Ib.

The halogen atom represented by X, Y and Z in the formula includes fluorine, chlorine, bromine and iodine atoms, and in particular, fluorine and chlorine atoms are preferred. The halogen atoms of these X, Y and Z may be identical or different.

The mono valent metal of group Ib represented by M in the formula includes silver, copper and gold, and in particular, silver and copper are preferred. For example, silver trifluoroacetate, cuprous trifluoroacetate, silver trichloroacetate, cuprous trichloroacetate, silver difluorochloroacetate, silver fluoro-dichloroacetate, etc. are mentioned. These salts may be used solely or in combination thereof. Among these salts, silver trihalogenacetates often separate silver deposits by means of light or radiation ray, and so it is desirable to treat the same in a dark place. In the case of cuprous salts it is desirable to take care relative to exposure of the salts to a strong oxidizing or reducing atmosphere and so preferably, to treat the same in system free from air, or in an inert atmosphere such as nitrogen, helium and argon.

The complex forming reaction between the trihalogenoacetate and hydrocarbons varies, depending upon the kinds of the hydrocarbons. Accordingly, the amount of the trihalogenoacetate to be used varies, depending upon the kinds of the respective hydrocarbons to be separated in the form of complexes, and at least a stoichiometric amount in the reaction of forming complexes with the hydrocarbons to be separated is required. The stoichiometric amount of the trihalogenoacetate required for the formation of complexes with the respective hydrocarbons is previously experimentally determined. If it is not required to separate entire amount of the desired hydrocarbons contained in the raw material mixture, the trihalogenoacetate is used in a smaller amount than the stoichiometric amount thereof, and if the desired hydrocarbons are to be obtained in a highly pure form, the amount of the trihalogenoacetate to be used is preferably larger than the stoichiometric amount thereof.

In general, the trihalogenoacetate is used in an amount of 0.5 – 2.0 times as much as the stoichiometric amount thereof required for the formation of complexes with hydrocabons to be separated.

The hydrocarbons to form complexes with the trihalogenoacetate are aromatic hydrocarbons substituted by hydrocarbyl groups, unsaturated aliphatic hydrocarbons, unsaturated cycloaliphatic hydrocarbons and condensed polycyclichydrocarbons.

The aromatic hydrocarbons substituted by hydrocarbyl groups are aromatic hydrocarbons having on the benzene nucleus thereof one or more alkyl, vinyl, cycloalkyl, aryl and aralkyl groups, and these groups may have a linear chain or branched chain, and the aryl group and the vinyl group may have further substituents. Representative examples of these aromatic hydrocarbons are, for example, toluene; $C_8$–$C_{10}$ aromatic hydrocarbons as shown in the following Table 1; $C_{11}$ alkyl-benzenes such as diisopropylbenzene; styrene; styrene derivatives such as $\alpha$-methyl-styrene, $\beta$-methyl-styrene, o-,m-,p-vinyl-toluene cis-, trans-stilbene, etc. In addition, cycloalkyl benzenes such as cyclohexyl-benzene and aryl substituted benzenes such as diphenyl derivatives, e.g., diphenyl, terphenyls, methyl-diphenyls, ethyl-diphenyls, isopropyl-diphenyls, etc. may also be used in the present invention.

TABLE 1

Ortho-xylene, para-xylene, meta-xylene,
isopropyl-benzene, 1-methyl-3-n-propylbenzene,
n-propyl-benzene, n-butyl-benzene,
1-methyl-3-ethylbenzene,  1-methyl-4-n-propylbenzene,
1-methyl-4-ethylbenzene, 1,2-diethylbenzene, 1,3,5-trimethylbenzene,
1,4-diethylbenzene, 1-methyl-2-ethylbenzene, 1,3-dimethyl-5-ethylbenzene,
t-butylbenzene, 1-methyl-2-n-propylbenzene, 1,2,4-trimethylbenzene,
1,4-dimethyl-2-ethylbenzene, isobutylbenzene, 1,3-dimethyl-4-ethylbenzene,
sec-butylbenzene, 1,2-dimethyl-4-ethylbenzene, 1-methyl-3-isopropylbenzene,
1,3-dimethyl-2-ethylbenzene, 1,2,3-trimethylbenzene,
1,2-dimethyl-3-ethylbenzene, 1-methyl-4-isopropyl-benzene,
1,2,4,5-tetramethylbenzene, 1-methyl-2-isopropyl-benzene,
1,2,3,5-tetramethylbenzene, 1,3-diethylbenzene,
1,2,3,4-tetramethylbenzene The unsaturated aliphatic hydrocarbons and the unsaturated cycloaliphatic hydrocarbons are olefinic hydrocarbons represented by the following formula:

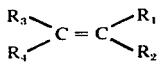

wherein $R_1$, $R_2$, $R_3$ and $R_4$ each represents hydrogen or an alkyl, cycloalkyl, alkenyl or cycloalkenyl group, and $R_2$ and $R_4$ may form an alkylene or alkenylene group and $R_1$ and $R_2$ may form an alkenylene group.

Representative example of these hydrocarbons are, for example, linear or branched mono-olefins such as ethylene, propylene, butene, iso-butene, heptene, hexene, pentene, 2-methyl-2-pentene, octene, etc.; polyolefins such as 1,3-butadiene, isoprene, 1,4-pentadiene, 1,2-pentadiene, 1,3-hexadiene, 1,5-hexadiene, octadiene, hexatriene, octatriene, etc.; cyclic olefins such as cyclopropene, cyclobutene, cylopentene, cyclohexene, cycloheptene, cyclobutadiene, cyclopentadiene, cyclohexadiene, cyclooctatriene, etc.; alkyl substituted cyclic olefins such as methyl-cyclopropene, methyl-cyclobutene, ethyl-cyclobutene, methyl-cyclohexene, etc. In addition, cycloalkyl substituted olefins such as vinylcyclohexane, vinylcyclohexene, etc. as well as methylenecylcopropane, methylenecyclohexane, etc., may also be mentioned.

The condensed polycyclic hydrocarbons contain 4 or more carbon atoms, and are for example, indene, naphthalene, azulene, methyl-naphthalene, ethyl-naphthalene, biphenylene, acenaphthylene, dimethyl-naphthalene, fluorene, phenalene, anthracene, phenanthrene, pyrene, chrysene, naphthacene, triphenylene, etc. as well as partially hydrogenated derivatives of these polycyclic hydrocarbons such as di-, tetra- and hexa-hydro derivatives thereof. In addition, these hydrocarbons may further be substituted by an alkyl group, a cycloalkyl group, an aryl group, an aralkyl group etc.

For the formation of complexes of the tri-halogenoacetate and these hydrocarbons, the trihalogenoacetate may be contacted with the liquid or gaseous hydrocarbons.

For example, to a liquid hydrocarbons is added the trihalogenoacetate and mixed. In this case, the mixture may be heated or cooled, if necessary. In general, however, the mixing may well be performed at normal temperature and the mixture is preferably somewhat stirred. The formed complexes are sometimes dissolved in excess hydrocarbons and sometimes are suspended. In the next place, after the excess hydrocarbons have been distilled off or the mixture has been cooled or otherwise a paraffin such as hexane or cyclohexane has been added to the mixture, the solid complexes may be separated. However, it is not always necessary to take out the complexes, and in this case, upon removing a part of impurities contained in the mixture, the formed complexes may be successively subjected to the next decomposition treatment. In addition, the existence of water on the formation of the complexes interferes with the formation, and so it is desired that the formation of the complexes is carried out in a dry state.

Another embodiment for forming hydrocarbon-trihalogenoacetate complexes is to introduce a gaseous material containing hydrocarbons into a column wherein a solid trihalogenoacetate or the trihalogenoacetate supported on a porous carrier such an alumina, silica, celite, titania, magnesia, pumice, active carbon, etc. has been filled, to form the desired complexes. In this introduction, the gaseous material is introduced at normal pressure or under a reduced pressure or in the presence of an inert gas carrier such as dried nitrogen gas, and if necessary, under heat. The temperature of the formation of the complexes may freely be selected in the scope ranging from low temperature to 200°C, and is preferably selected in the range of 0° – 120° C. In some cases, the complex forming reaction is an exothermic reaction, and in such cases, it is necessary to cool the reaction system by appropriate means and to keep the temperature thereof constant.

The thus formed complexes may easily be decomposed by heating or bringing the same into contact with water thereby to release the trihalogenoacetate and hydrocarbons. For example, when the complexes of silver trihalogenoacetate are put into water at normal temperature, the complexes are decomposed and the released silver trihalogenoacetate is dissolved in water, and the hydrocarbons are separated as an oil layer or crystals. The thus freed hydrocarbons are separated or extracted by using a solvent such as paraffin whereby the hydrocarbons are recovered and collected. The silver trihalogenoacetate may easily be recovered and collected by distilling out the water. Or otherwise, the complexes may be decomposed by contacting the same with steam. In the latter case, the silver trihalogenoacetate remains as a solid, and the hydrocarbons only flow out together with the steam. Accordingly, by repeatedly operating the formation of complexes where a gaseous mixture containing hydrocarbons is introduced into a column filled with a carrier to which a trihalogenoacetate has been adsorbed and the decomposition of the formed complexes to follow where steam is introduced into the column, the hydrocarbons may continuously be separated. On the other hand, when a cuprous trifluoroacetate - complex is contacted with water, a disproportionation reaction of cuprous ion into cupric ion and metal occurs. However, the cuprous trifluoroacetate may be recovered as another complex by removing the water by means of an azeotropic distillation.

For example, after the water decomposition of the complex, to the resulting aqueous solution containing the cuprous salt is added another hydrocarbon and subjected to the azeotropic distillation thereby to remove water and form a complex of the cuprous salt and the another hydrocarbon. Then the thus formed complex is collected.

Accordingly, it is preferable to use the same hydrocarbon as to be separated according to the present method in the course of the azeotropic distillation since the formed complex during the azeotropic distillation is the same complex of the hydrocarbons to be separated and these can be recycled to the water decomposition step.

In any case as mentioned above, the amount of water to be used is not limited, and is, in general, applied in a molar ratio from 1 to 500 to the tri-halogenoacetate in the complexes. However, if the amount of the water is too much, such is not preferable from an economical viewpoint in that the recovering step of the trihalogenoacetate would become expensive. Accordingly, water is preferably used in a mole ratio from 1 to 100, more preferably 3 to 50.

The treating temperature is not so high, since if the temperature is too high, decomposition of the hydrocarbons themselves to be separated or coloration thereof would sometimes occur. In general, the temperature is selected in the range of 0° – 200° C, preferably 0° – 130° C.

As mentioned above, the complex forming ability between the trihalogenoacetate and the hydrocarbons varies depending upon the structures of the hydrocarbons. Accordingly, by utilizing the difference and by appropriately selecting the operating conditions or by repeating the complex formation, complexes of specific hydrocarbons may selectively be formed and thus the specified hydrocarbons may be separated and collected.

For example, with respect to the xylene-complex forming ability between xylene and the silver trihalogenoacetate, orthoxylene has the highest ability, and para-xylene, meta-xylene and ethyl-benzene have gradually lower abilities in this order. Accordingly, it is possible to selectively separate the orthoxylene as the xylene-complex from a mixed xylene or from a mixture of xylene and other hydrocarbons, or it also is possible to separate the ortho-xylene from the mixed xylene at first, and in the next place, to separate the para-xylene from the residue and then analogously to separate the meta-xylene and the ethylbenzene in this order. In this separation, if the purity of the specified concentrated component in the separated xylene is not sufficiently high, the purity may easily be improved by repeatedly performing the formation of the tri-halogenoacetate complexes.

With respect to styrene groups, the complex forming ability between the styrene groups and the trihalogenoacetate is stronger than that of other aromatic hydrocarbons, and thus the styrene groups preferentially form the complexes. Accordingly when a mixture of ethylbenzene and styrene is used, the styrene almost selectively forms a complex.

In addition, the complex forming ability also varies depending upon the kinds of isomers, and thus, it is possible to separate a mixture of cis- and trans-isomers of stilbene or a mixture of o-, m- and p-isomers of vinyl-toluene into the respective pure isomers, by utilizing the difference of the complex forming ability thereof with the trihalogenoacetate. Furthermore, it also is possible to separate the desired styrene from other hydrocarbons contained in the styrene mixture of to separate the desired styrene isomer from other isomers and further to increase the purity of the separated styrene by repeatedly performing the complex formation. In addition, it also is possible to successively separate 2,6-dimethyl-, 1,6-dimethyl-, 1,2-dimethyl and 2,3-dimethyl-naphthalene isomers contained in a tar which is called a methyl-naphthalene fraction or in a mixture of petroleum products, or to mutually separate α- and β-methylnaphthalenes from each other. Moreover it further is possible to separate naphthalene and the partial hydrogenated product thereof, tetralin, from each other, or to separate anthracene and phenanthrene isomers from each other. In addition, the present invention may be adapted for other various uses, say as follows: Successive separation and collection of butadiene, 1-butene, cis- and trans-2-butenes and isobutylene from a $C_4$ fraction which is called a BB fraction; separation and collection of dienes such as cyclobutadiene, piperylene, isoprene, etc. and various kinds of monoolefin isomers from $C_5$ fraction; separation of 1,4-cyclohexadiene from a reaction mixture thereof prepared by electrolytic reduction of benzene; mutual separation of benzene, cyclohexene, cyclohexane, etc.

The method of the present invention may be combined with the conventional separation method of condensed polycyclic hydrocarbons which has hitherto been proposed. For example, when the present invention is applied on the distilled and fractionated product, the cooled and separated product, the recrystallized product, etc., it is possible to increase the purities of these products. For example, it, of course, is possible to use petroleum reformates, cracked gasolines, isomer mixtures obtained from the alkylation of benzene or toluene, etc. as the raw materials of aromatic hydrocarbons and to directly adapt the method of the present invention for the raw materials. Apart from this, it also is possible to previously separate one or more aromatic hydrocarbons from aromatic hydrocarbon mixtures by means of the conventional distillation method, separation method, solvent extraction method or the like which has hitherto been proposed, and afterwards to separate the respective components by applying the method of the present invention. Or otherwise, after one or more aromatic hydrocarbons have previously been separated by means of the method of the present invention, and afterwards the conventional distillation method, separation method, solvent extraction method or the like may be combined with the former method thereby to separate the respective components. The combination of the present method and the conventional method is appropriately determined from the relative difficulty of the process and economical viewpoint.

In addition, when hydrocarbons of high polymerizability are to be treated, it also is possible to perform the present process under the presence of a phenol series or amine series polymerization inhibitor, for the purpose of inhibiting the polymerization of the hydrocarbons used.

Now, the present invention will be explained more in detail by the following examples; which, however, do not whatsoever limit the scope of the present invention.

EXAMPLE 1 to 0.95 g of mixed xylene consisting of 22.4% of ethylbenzene, 23.4% of para-xylene, 25.3% of meta-xylene and 28.6% of ortho-xylene, 0.961 g of silver trifluoroacetate ($CF_3CO_2$-Ag) was added at room temperature, whereby the silver salts were dissolved. In the next place, the excess xylene was distilled out under a reduced pressure of 5 mmHg to obtain 1.201 g of white powders.

To these powders, 10 ml of water was added, whereby the powders were dissolved and the xylene was separated as an oily material. The separated xylene was analyzed by means of gas chromatography, and the result was as follows:

| | |
|---|---|
| ethyl-benzene | 5.7% |
| para-xylene | 15.3% |
| meta-xylene | 5.7% |
| ortho-xylene | 73.3% |

It was confirmed from the result that the ortho-xylene was concentrated.

EXAMPLE 2

To 1.31 g of mixed xylene consisting of 33.1% of ethylbenzene, 33.7% of para-xylene and 33.1% of meta-xylene, 0.848 g of silver trifluoroacetate ($CF_3CO_2$-Ag) was added at 60° C, whereby the silver salts were dissolved. In the next place, the excess xylene was distilled out under a reduced pressure of 5 mmHg to obtain 1.104 g of white powders.

To these powders, 10 ml of water was added, whereby the powders were dissolved and the xylene was separated as an oily material. The separated xylene was analyzed by means of gas chromatography and the result was as follows:

| | |
|---|---|
| ethyl-benzene | 10.4% |
| para-xylene | 62.9% |
| meta-xylene | 26.6% |

EXAMPLE 3

To 1.91 g of the same mixed xylene as in Example 1, 1.147 g of silver trichloroacetate ($CCl_3$—$CO_2$—Ag) was added at room temperature, and then the excess xylene was distilled out under a reduced pressure of 5 mmHg to obtain 1.403 g of white powders.

To these powders, 10 ml of water was added, whereby the powders were dissolved and the xylene was separated as an oily material. The separated xylene was analyzed by means of gas chromatography, and the result was as follows:

| | |
|---|---|
| ethyl-benzene | 2.5% |
| para-xylene | 31.7% |
| meta-xylene | 15.6% |
| ortho-xylene | 50.3% |

EXAMPLE 4

To 1.91 g of the same mixed xylene as in Example 1, 0.710 g of cuprous trichloroacetate was added at 100° C, and then the excess xylene was distilled out at room temperature under a reduced pressure of 5 mmHg to obtain 0.915 g of powders.

To these powders, 10 ml of water was added, whereby the powders were dissolved and the xylene was separated as an oily material. The separated xylene was analyzed by means of gas chromatography and the result was as follows:

| | |
|---|---|
| ethyl-benzene | 7.1% |
| para-xylene | 14.5% |
| meta-xylene | 21.8% |
| ortho-xylene | 56.6% |

Comparative Example

In the above mentioned Example 1, $FCH_2$—$CO_2$—Ag, $Cl_2CHCO_2$—Ag, $ClCH_2$—$CO_2$—Ag, $CH_3$—$CO_2$—Ag and $(CH_3)_3$—C—$CO_2$—Ag were used in place of the silver trifluoroacetate.

However in the compounds used, little complex forming ability and further little difference in the complex forming ability of the isomers could be found.

EXAMPLE 5

To 3.32 g of a mixture consisting of 50% of styrene and 50% of ethyl-benzene, 0.85 g of silver trifluoroacetate was dissolved at room temperature, and then the excess styrene and ethyl-benzene were distilled out under a reduced pressure of 3 mmHg to obtain 1.17 g of white solid. To this solid, 10 ml of water was added, whereby the solid was dissolved and an oily material was separated. The oily material was analyzed by means of gas chromatography, whereby it was confirmed that the composition consisted of 94.4% of styrene and 5.6% of ethyl-benzene. The yield was 0.32 g.

Apart from the respective silver salts of acetic acid, mono-chloroacetic acid, di-chloroacetic acid were used in place of the silver trifluoroacetate. However, no complex was formed under the condition.

EXAMPLE 6

To 3.32 g of a mixture consisting of equal amount of styrene and p-xylene, 0.71 g of cuprous trifluoroacetate ($CF_3$—$CO_2$—Cu) was added at room temperature and then, the excess hydrocarbon was distilled out under a reduced pressure of 3 mmHg to obtain 1.04 g of white solid.

To this solid, 10 ml of water was added. Then, the separated oily material was extracted by cyclohexane and was analyzed by means of gas chromatography, whereby it was confirmed that the oily composition consisted of 98.5% of styrene and 1.5% of p-xylene. The yield was 0.42 g.

EXAMPLE 7

To 3.30 g of a mixture consisting of 50% of styrene, 33% of m-xylene and 17% of p-xylene, 0.99 g of silver trichloroacetate was added at room temperature and then the excess material was distilled out under a reduced pressure of 3 mmHg to obtain 1.30 g of white solid. To this solid, 10 ml of water was added, whereby the solid was dissolved and an oily material was separated as an upper layer. The oily material was extracted by hexane and analyzed by means of gas chromatography. It was confirmed that the oily material consisted of 93.2% of styrene. The yield was 0.31 g.

EXAMPLE 8

Into 30 ml of water solution containing 2.0 g of silver trifluoroacetate, was immersed 10 ml of 50 mesh pumice and then was dried in the dark at 100° C. Afterwards, it was packed into a glass column having a diameter of 18 mm and was heated to 100° C in a stream of a nitrogen. 2.20 g of composition consisting of an equal amount of styrene and ethyl-benzene together with nitrogen was provided through the packed column for 30 minutes and further nitrogen was passed thereinto for 5 minutes. During this, the effluent was cooled and collected to obtain 1.17 g of a material consisting of 19.4% of styrene and 80.6% of ethylbenzene. To the packed layer, 20 ml of steam together with nitrogen was passed for 30 minutes and the effluent was cooled and collected. Then, the effluent was extracted by cyclohexane and analyzed, whereby it was confirmed that the composition consisted of 85.1% of styrene and 14.9% of ethyl-benzene. The yield was 0.95 g.

EXAMPLE 9

To 6.0 g of cracked gasoline consisting of 21.6% of styrene, 5.3% of ethyl-benzene, 23.0% of a xylene mixture, 28.3% of toluene, 1.8% of benzene and 19.8% of others, 1.40 g of cuprous trifluoroacetate was mixed at room temperature, and then the excess hydrocarbon was distilled out under a reduced pressure of 3 mmHg to obtain 2.25 g of white solid. To this solid, 20 ml of water was added, whereby an oily material was separated. Then the separated oily material was extracted by cyclohexane and was analyzed by means of gas chromatography. It was confirmed that the oily material contained 78.3% of styrene. The yield was 0.83 g.

EXAMPLE 10

To 3.50 g of a mixture consisting of an equal amount of α-methylstyrene and cumene, 0.85 g of silver trifluoroacetate was added at room temperature, and then the excess material was distilled out under a reduced pressure of 3 mmHg to obtain a white solid. To this material, 10 ml of water was added and then an oily material was extracted by hexane. The oily material was analyzed by means of gas chromatography, whereby it was confirmed that it contained 96.8% of α-methylstyrene. The yield was 0.37 g.

EXAMPLE 11

To 2.67 g of a mixture consisting of 29.7% of p-vinyltoluene and 70.3% of m-vinyltoluene, 0.82 g of silver trifluoroacetate was dissolved and then, the excess hydrocarbon was distilled out under a reduced pressure of 1 mmHg to obtain 1.12 g of an oily material. To the material, 10 ml of water was added to obtain 0.31 g of an oily material. Then it was analyzed by means of gas chromatography, whereby it was confirmed that it was a mixture consisting of 33.9% of p-vinyltoluene and 66.1% of m-vinyltoluene.

Apart from this, 0.82 g of silver trifluoroacetate was recovered from the aqueous solution after removing the water.

EXAMPLE 12

To 2.20 g of a mixture consisting of 50.0% of 1,2,3,5-tetramethylbenzene (isodurene) and 50.0% of 1,2,4,5-tetramethylbenzene (durene), 0.88 g of silver trifluoroacetate was mixed at 50° C. Then, the excess tetramethylbenzene was distilled out under a reduced pressure at 50° C to obtain 1.40 g of residue. To this residue, 10 ml of water and 5 ml of n-hexane were added and shaken. The n-hexane layer was analyzed by means of an infrared-spectrophotometer to obtain the following result.

| | |
|---|---|
| 1,2,4,5-tetramethylbenzene | 69.7% |
| 1,2,3,5-tetramethylbenzene | 30.3% |

EXAMPLE 13

2.43 g of a mixture consisting of 36.6% of n-butylbenzene, 32.7% of iso-butylbenzene, and 30.7% of tert.-butylbenzene and 0.65 g of silver trifluoroacetate were mixed at 90° C, whereby the silver salts were dissolved. Then the excess butylbenzene was distilled out under the reduced pressure of 0.6 mmHg to obtain 0.93 g of powders. To these powders, 10 ml of water was added and an oily material was separated. The oily material was analyzed by means of gas chromatography to obtain the following result.

| | |
|---|---|
| n-butylbenzene | 70.5% |
| iso-butylbenzene | 13.9% |
| tert.-butylbenzene | 15.6% |

EXAMPLE 14

To 1.04 g of a cymene mixture consisting of 51.3% of p-cymene and 48.7% of m-cymene, 0.61 g of cuprous trifluoroacetate was added and mixed at 70° C. Then the excess cymene was distilled out at room temperature under a reduced pressure of 5 mmHg to obtain 0.85 g of white powders. To these powders, 10 ml of water was added, whereby an oily material was separated. The oily material was extracted by cyclohexane and analyzed by means of gas chromatography to obtain the following result.

| | |
|---|---|
| p-cymene | 45.6% |
| m-cymene | 54.4% |

EXAMPLE 15

In the process of the above-mentioned Example 14, 0.94 g of silver trichloroacetate was used in place of cuprous trifluoroacetate. The result was as follows:

| | |
|---|---|
| p-cymene | 43.1% |

| | |
|---|---|
| m-cymene | 56.9% |

EXAMPLE 16

To 2.92 g of a mixture consisting of 31.9% of 1,2,3-trimethylbenzene, 34.6% of 1,2,4-trimethylbenzene and 33.5% of 1,3,5-trimethylbenzene, 0.872 g of silver trifluoroacetate was mixed and dissolved. Then, the excess trimethylbenzene was distilled off to obtain 1.176 g of white powders. To these powders, 10 ml of water was added, whereby an oily material was separated. The oily material was extracted by n-hexane and analyzed by means of gas chromatography to obtain the following result.

| | |
|---|---|
| 1,2,3-trimethylbenzene | 51.4% |
| 1,2,4-trimethylbenzene | 42.4% |
| 1,3,5-trimethylbenzene | 6.2% |

EXAMPLE 17

To 1.87 g of a mixture consisting of 33.4% of cyclohexene, 32.8% of 1,4-cyclohexadiene and 33.7% of benzene, 0.690 g of cuprous trifluoroacetate was mixed at 60° C. Then the excess $C_6$ compound was distilled out under a reduced pressure of 50 mmHg to obtain 1.082 g of powders. To these powders 10 ml of water was added, whereby 0.40 g of oily material was separated. The oily material was analyzed by means of gas chromatography to obtain the following result.

| | |
|---|---|
| cyclohexene | 0.5% |
| 1,4-cyclohexadiene | 66.5% |
| benzene | 33.0% |

EXAMPLE 18

To 0.67 g of a mixture consisting of 48.5% of n-1-hexene and 51.5% of n-2-hexene, 0.427 g of silver trifluoroacetate was mixed at room temperature, whereby the silver salts were dissolved. Then, the excess hexene was distilled out under a reduced pressure of 10 mmHg to obtain 0.552 g of oily material. To this material, 10 ml of water and 5 ml of benzene were added and shaken. The benzene layer was analyzed by means of gas chromatography to obtain the following result.

| | |
|---|---|
| n-1-hexene | 54.2% |
| n-2-hexene | 45.8% |

EXAMPLE 19

To 1.03 g of a mixture consisting of 51.8% of 1,3-pentadiene, and 48.2% of 2-methyl-1,3-butadiene, 0.864 g of silver trifluoroacetate was mixed at 10° C, whereby the silver salts were dissolved. Then the excess $C_5$ compound was distilled out under a reduced pressure of 100 mmHg to obtain 1.022 g of white powders. To these powders, 10 ml of water and 5 ml of n-hexane was added and shaken. The n-hexane layer was analyzed by means of gas chromatography to obtain the following result.

| | |
|---|---|
| 1,3-pentadiene | 66.7% |
| 2-methyl-1,3-butadiene | 33.3% |

EXAMPLE 20

1.82 g of a mixture consisting of 51.6% of indane and 48.4% of indene and 0.93 g of silver trifluoroacetate were mixed at 50° C, whereby almost all of the silver salt was dissolved. Then the mixture was cooled to room temperature and 10 ml of n-hexane was added, whereby crystals were deposited. The filtered crystals were washed by n-hexane and 10 ml of water was added thereto, whereby an oily material was separated. The oily material was dissolved n-hexane and the resulting solution was analyzed by means of gas chromatography to obtain the following result.

| | |
|---|---|
| indane | 12.1% |
| indene | 87.9% |

EXAMPLE 21

0.75 g of a mixture consisting of 26.3% of 1,6-dimethylnaphthalene, 39.8% of 2,6-dimethyl-naphthalene and 33.9% of 2,3-dimethyl-naphthalene and 0.186 g of silver trifluoroacetate were mixed at 80° C and then the mixture was treated in the same manner as in Example 20. The material was analyzed by means of gas chromatography to obtain the following result.

| | |
|---|---|
| 1,6-dimethyl-naphthalene | 7.1% |
| 2,6-dimethyl-naphthalene | 90.6% |
| 2,3-dimethyl-naphthalene | 2.3% |

EXAMPLE 22

3.28 g of a mixture consisting of 29.7% of α-methyl-naphthalene and 70.3% of β-methyl-naphthalene and 0.92 g of silver trifluoroacetate were mixed at 80° C and was treated in the same manner as in Example 20. The material was analyzed by means of gas chromatography to obtain the following result.

| | |
|---|---|
| α-methyl-naphthalene | 23.7% |
| β-methyl-naphthalene | 76.3% |

EXAMPLE 23

To 1.30 g of a mixture consisting of 48.8% of acenaphthene and 51.2% of fluorene, 0.565 g of cuprous trifluoroacetate (a reaction product of trifluoroacetate with cuprous oxide) was mixed at 60° C and then 10 ml of n-hexane was added to this mixture to deposit crystals. Filtered crystals were washed by n-hexane. To these crystals, 10 ml of water and 5 ml of n-hexane were added and shaken to form an n-hexane layer.

The n-hexane layer was analyzed by means of gas chromatography to obtain the following result.

| | |
|---|---|
| acenaphthene | 82% |
| fluorene | 18% |

EXAMPLE 24

To 2.10g of a mixture consisting of 50% of naphthalene and 50% of tetralin, 1.09 g of silver trichloroacetate was added and stirred. Then it was treated in the same manner as in Example 23 to obtain an n-hexane layer. The n-hexane layer was analyzed by means of gas chromatography to obtain the following result.

| | |
|---|---|
| naphthalene | 95.7% |
| tetralin | 4.3% |

While the invention has been described in detail and with reference to specific embodiments thereof, it will be apparent to one skilled in the art that various changes and modifications can be made therein without departing from the spirit and scope thereof.

What we claim is:

1. A method for separating hydrocarbons which comprises reacting a mixture containing hydrocarbons under substantially anhydrous conditions with a trihalogenoacetate of the formula

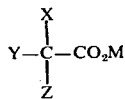

wherein X, Y and Z each represents a halogen atom and M represents a monovalent metal of Group Ib to form complexes, separating the formed complexes as a solid from the mixture which also contains non-complexed hydrocarbons by distillation, and then decomposing the solid complexes by bringing the same into contact with water to separate the desired hydrocarbons, wherein said hydrocarbons are selected from the group consisting of aromatic hydrocarbons substituted by hydrocarbyl groups and condensed polycyclic hydrocarbons.

2. The method as claimed in claim 1 where the substituents X, Y and Z in the formula are selected from the group consisting of fluorine and chlorine atoms.

3. The method as claimed in claim 1 where the metal M is selected from the group consisting of silver and copper.

4. The method as claimed in claim 1 where the trihalogenoacetate is selected from the group consisting of silver trifluoroacetate, cuprous trifluoroacetate, silver trichloroacetate, cuprous trichloroacetate, silver difluoro-chloroacetate and silver fluorodichloroacetate.

5. The method as claimed in claim 1 where about the stoichiometric amount of the trihalogenoacetate is used.

6. The method as claimed in claim 1 where the aromatic hydrocarbons substituted by hydrocarbyl groups are ones containing on the benzene nucleus thereof one or more members selected from the group consisting of alkyl, vinyl, cycloalkyl, aryl and aralkyl groups.

7. The method as claimed in claim 1 where the condensed polycyclic hydrocarbons are ones containing at least four carbon atoms, and are selected from the group consisting of indene, naphthalene, azulene, methyl-naphthalene, ethyl-naphthalene, biphenylene, acenaphthylene, dimethylnaphthalene, fluorene, phenalene, anthracene, phenanthrene, pyrene, chrysene, naphthacene, triphenylene and partially hydrogenated compounds of these polycyclic hydrocarbons selected from the group consisting of di-, tetra- and hexa-hydro derivatives thereof.

8. The method as claimed in claim 1 where the water is used in more than the amount equimolar to the trihalogenoacetate forming the complex.

9. The method as claimed in claim 1 where a mixture containing at least two kinds of $C_8$-aromatic hydrocarbons selected from the group consisting of ortho-xylene, meta-xylene, para-xylene, ethylbenzene and styrene is reacted with the trihalogenoacetate to form complexes, then the formed complexes are separated from the mixture and decomposed with water to free the $C_8$-aromatic hydrocarbons whereby the aromatic hydrocarbons are separated from each other due to the structural differences thereof.

10. The method as claimed in claim 9 where the mixture contains styrene and ethyl benzene.

11. The method as claimed in claim 1 where the amount of the trihalogenoacetate is in the range of 0.5–2.0 times the hydrocarbons.

12. The method as claimed in claim 1 where the formed complexes are decomposed by contacting with steam.

13. The method as claimed in claim 1 wherein following contact of the complex with water to accomplish decomposition the hydrocarbons separate as an oily layer and the trihalogenoacetate separates in said water.

14. The method as claimed in claim 1 wherein following contact of the complex with water to accomplish decomposition the hydrocarbons separate as crystals of hydrocarbons and the trihalogenoacetate separates in said water.

15. The method of claim 12 wherein following contact of said complex with said steam to accomplish decomposition the trihalogenoacetate separates in solid form and said hydrocarbons are carried in said steam.

16. The method for separating methyl naphthalenes where a mixture of α-methyl naphthalene and β-methyl naphthalene is reacted with silver tri-fluoroacetate to form complexes of β-methyl naphthalene, then the formed complexes are separated from the mixture and decomposed with water to free β-methyl naphthalene.

17. The method for separating dimethyl naphthalene where a mixture of 1,6-, 2,6-, and 2,3-dimethyl naphthalene is reacted with silver tri-fluoroacetate to form complexes of 2,6-dimethyl naphthalene selectively, then the formed complexes are separated and decomposed with water to separate 2,6-dimethyl naphthalene.

18. The method for separating hydrocarbons which comprises reacting a mixture containing at least one kind of hydrocarbon selected from the group consisting of aromatic hydrocarbons substituted by one or more hydrocarbyl groups and condensed polycyclic hydrocarbons in the gaseous phase under substantially anhydrous conditions with a trihalogenoacetate of the following formula

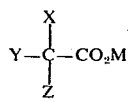

wherein X, Y and Z are the same or different and each represents a halogen atom and M represents a monovalent metal of Group Ib, which is solid or supported on a porous carrier, to form solid complexes, then the formed complexes are decomposed by contacting with steam to separate hydrocarbons and the separated hydrocarbons are collected.

19. A method for separating hydrocarbons which comprises reacting a mixture containing hydrocarbons under substantially anhydrous conditions with a trihalogenoacetate of the formula

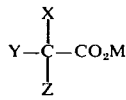

wherein X, Y and Z each represents a halogen atom and M represents a monovalent metal of Group Ib to form complexes, separating the formed complexes as a solid from the mixture which also contains non-complexed hydrocarbons by cooling, and then decomposing the solid complexes by bringing the same into contact with water to separate the desired hydrocarbons, wherein said hydrocarbons are selected from the group consisting of aromatic hydrocarbons substituted by hydrocarbyl groups and condensed polycyclic hydrocarbons.

20. The method as claimed in claim 19, where the substituents X, Y and Z in the formula are selected from the group consisting of fluorine and chlorine atoms.

21. The method as claimed in claim 19, where the metal M is selected from the group consisting of silver and copper.

22. The method as claimed in claim 19, where the trihalogenoacetate is selected from the group consisting of silver trifluoroacetate, cuprous trifluoroacetate, silver trichloroacetate, cuprous trichloroacetate, silver difluorochloroacetate and silver fluorodichloroacetate.

23. The method as claimed in claim 19, where about the stoichiometric amount of the trihalogenoacetate is used.

24. The method as claimed in claim 19, where the aromatic hydrocarbons substituted by hydrocarbyl groups are ones containing on the benzene nucleus thereof one or more members selected from the group consisting of alkyl, vinyl, cycloalkyl, aryl and aralkyl groups.

25. The method as claimed in claim 19, where the condensed polycyclic hydrocarbons are ones containing at least four carbon atoms, and are selected from the group consisting of indene, naphthalene, azulene, methyl-naphthalene, ethylnaphthalene, biphenylene, acenaphthylene, dimethylnaphthalene, fluorene, phenalene, anthracene, phenanthrene, pyrene, chrysene, naphthacene, triphenylene and partially hydrogenated compounds of these polycyclic hydrocarbons selected from the group consisting of di-, tetra- and hexa-hydro derivatives thereof.

26. The method as claimed in claim 19, where a mixture containing at least two kinds of $C_8$-aromatic hydrocarbons selected from the group consisting of ortho-xylene, meta-xylene, para-xylene, ethylbenzene and styrene is reacted with the trihalogenoacetate to form complexes, then the formed complexes are separated from the mixture and decomposed with water to free the $C_8$-aromatic hydrocarbons whereby the aromatic hydrocarbons are separated from each other due to the structural differences thereof.

27. The method as claimed in claim 19, where the amount of the trihalogenoacetate is in the range of 0.5–2.0 times the hydrocarbons.

28. The method as claimed in claim 19, where the formed complexes are decomposed by contacting with steam.

29. The method as claimed in claim 19, wherein following contact of the complex with water to accomplish decomposition the hydrocarbons separate as an oily layer and the trihalogenoacetate separates in said water.

30. The method as claimed in claim 19, wherein following contact of the complex with water to accomplish decomposition the hydrocarbons separate as crystals of hydrocarbons and the trihalogenoacetate separates in said water.

31. A method for separating hydrocarbons which comprises reacting a mixture containing hydrocarbons under substantially anhydrous conditions with a trihalogenoacetate of the formula

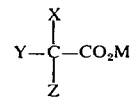

wherein X, Y and Z each represents a halogen atom and M represents a monovalent metal of Group Ib to form complexes, separating the formed complexes as a solid from the mixture which also contains non-complexed hydrocarbons by addition of a solvent unable to form complexes with the trihalogenoacetate, and then decomposing the solid complexes by bringing the same into contact with water to separate the desired hydrocarbons, wherein said hydrocarbons are selected from the group consisting of aromatic hydrocarbons substituted by hydrocarbyl groups and condensed polycyclic hydrocarbons.

32. The method as claimed in claim 31, where the substituents X, Y and Z in the formula are selected from the group consisting of fluorine and chlorine atoms.

33. The method as claimed in claim 31, where the metal M is selected from the group consisting of silver and copper.

34. The method as claimed in claim 31, where the trihalogenoacetate is selected from the group consisting of silver trifluoroacetate, cuprous trifluoroacetate, silver trichloroacetate, cuprous trichloroacetate, silver difluorochloroacetate and silver fluorodichloroacetate.

35. The method as claimed in claim 31, where about the stoichiometric amount of the trihalogenacetate is used.

36. The method as claimed in claim 31, where the aromatic hydrocarbons substituted by hydrocarbyl groups are ones containing on the benzene nucleus thereof one or more members selected from the group consisting of alkyl, vinyl, cycloalkyl, aryl and aralkyl groups.

37. The method as claimed in claim 31, where the condensed polycyclic hydrocarbons are ones contaning at least four carbon atoms, and are selected from the group consisting of indene, naphthalene, azulene, methyl-naphthalene, ethylnaphthalene, biphenylene, acenaphthylene, dimethylnaphthalene, fluorene, phenalene, anthracene, phenanthrene, pyrene, chrysene, naphthacene, triphenylene and partially hydrogenated compounds of these polycyclic hydrocarbons selected from the group consisting of di-, tetra- and hexa-hydro derivatives thereof.

38. The method as claimed in claim 31, where a mixture containing at least two kinds of $C_8$-aromatic hydrocarbons selected from the group consisting of ortho-xylene, meta-xylene, para-xylene, ethylbenzene and styrene is reacted with the trihalogenoacetate to form complexes, then the formed complexes are separated from the mixture and decomposed with water to free the $C_8$-aromatic hydrocarbons whereby the aromatic hydrocarbons are separated from each other due to the structural differences thereof.

39. The method as claimed in claim 31, where the amount of the trihalogenoacetate is in the range of 0.5–2.0 times the hydrocarbons.

40. The method as claimed in claim 31, where the formed complexes are decomposed by contacting with steam.

41. The method as claimed in claim 31, wherein following contact of the complex with water to accomplish decomposition the hydrocarbons separate as an oily layer and the trihalogenoacetate separates in said water.

42. The method as claimed in claim 31, wherein following contact of the complex with water to accomplish decomposition the hydrocarbons separate as crystals of hydrocarbons and the trihalogenoacetate separates in said water.

* * * * *